United States Patent [19]

Mochizuki et al.

[11] 4,411,520

[45] Oct. 25, 1983

[54] LIGHT DISPERSION MEASURING APPARATUS

[75] Inventors: Kiyofumi Mochizuki, Yokohama; Hiroharu Wakabayashi, Kawasaki; Yasuhiko Niiro, Yokohama, all of Japan

[73] Assignee: Kokusai Denshin Denwa Kabushiki Kaisha, Tokyo, Japan

[21] Appl. No.: 222,973

[22] Filed: Jan. 7, 1981

[30] Foreign Application Priority Data

Jan. 14, 1980 [JP] Japan .................................. 55-2872

[51] Int. Cl.³ .......................................... G01N 21/00
[52] U.S. Cl. .................................................. 356/73.1
[58] Field of Search ................ 356/73.1; 307/425, 428

[56] References Cited

U.S. PATENT DOCUMENTS 3,778,635 12/1973 Givliani .............................. 307/425

OTHER PUBLICATIONS

Gulyaev et al., Sov. J. Quantum Electron., vol. 7, #11, pp. 1410–1411.
Bareika et al., "Parametric Genot Tunable ps Light Pulses in the 3.7–10.2 μm Range", Sov. Tech. Phys. Lett, vol. 6, #6, pp. 301–302, Jun. 1980.

*Primary Examiner*—Vincent P. McGraw
*Assistant Examiner*—L. Dietert
*Attorney, Agent, or Firm*—Robert E. Burns; Emmanuel J. Lobato; Bruce L. Adams

[57] ABSTRACT

A light dispersion measuring apparatus, provided with a light source for generating reference light pulses of short duration and of a constant frequency and also variable-frequency light pulses in synchronization with the reference light pulses but at a frequency different therefrom. A variable optical delay line delays the reference light pulses. An optical transmission medium, to be detected and to which the variable-frequency light pulses are applied is provided. An optical non-linear effect element receiver the output light pulses from the variable optical delay line and the optical transmission medium and is disposed so that when the two light pulses coincide emitted from the light source with each other, the sum component of the frequencies of the two types of light pulses produces a maximum output. A photo detector detects the sum component. Light dispersion in the optical transmission medium being measured from the delay of the variable optical delay line is adjusted so that the sum components yields a maximum output with respect to the frequency of the variable-frequency light pulses. The frequency of the reference light pulses can be made to be equal to the variable-frequency of the variable-frequency light pulses.

3 Claims, 5 Drawing Figures

LIGHT DISPERSION MEASURING APPARATUS

FIELD OF THE INVENTION

The present invention relates to a light dispersion measuring apparatus which has a picosecond resolution.

BACKGROUND OF THE INVENTION

The wavelength of light and the repeater intervals for repeating and transmitting light in optical fiber communications are dependent on the transmission loss and the band characteristic of the optical fiber used. Especially, the dispersion characteristic of the optical fiber causes a waveform distortion, thereby imposing a limitation on the transmission rate in digital transmission. Accordingly, even if an optical fiber of an extremely small loss is employed, the repeater intervals may sometimes be limited by the dispersion characteristic of the optical fiber; therefore, measurement of the dispersion characteristic of the optical fiber is very important as is the case with measurement of the transmission loss. These measurements are usually conducted, using a small-length fiber, and the measured values are applied to a large-length fiber on the basis of the ratio of length, so that even a small measurement error in the small-length fiber will produce a large error in determining the dispersion characteristic of the large-length fiber. For the reason mentioned above, a measuring apparatus with a sufficiently high accuracy is required for measuring the dispersion characteristic of the small-length fiber.

However, conventional measuring apparatus cannot be employed as described below for measurements in wavelength of 1.3 $\mu$m and 1.5 $\mu$m bands which are regarded as promising for optical fiber communications.

SUMMARY OF THE INVENTION

In view of the abovesaid defects of the prior art, an object of the present invention is to provide a light dispersion measuring apparatus which employs a nonlinear crystal in place of a Kerr shutter and in which light having passed through an optical transmission medium is converted to light of a wavelength detectable by a photo detector for measurement.

BRIEF DESCRIPTION OF THE ACCOMPANYING DRAWINGS

The invention will be described in detail below with reference to the accompanying drawings, in which:

FIG. 1 is a schematic diagrams showing an example of a conventional light dispersion measuring apparatus; and FIGS. 2, 3A, 3B and 4 are schematic diagrams illustrating embodiments of the present invention.

DETAILED DESCRIPTION

To make differences between prior art and the present invention clear, an example of conventional systems will first be described.

Figure 1:
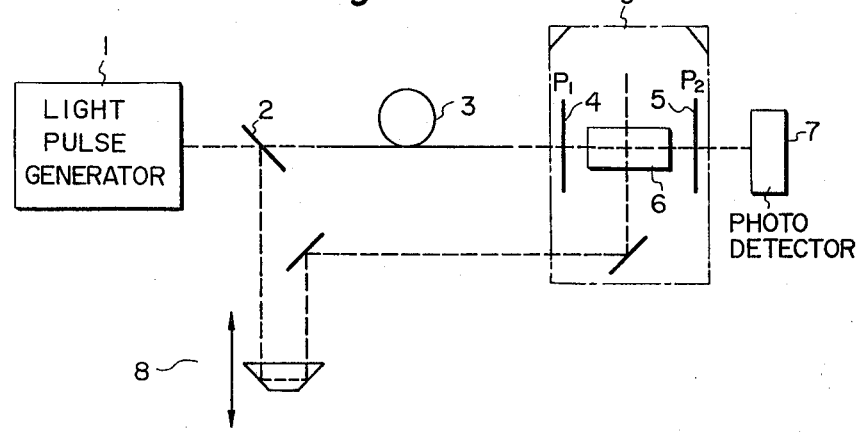

A conventional measuring apparatus of this kind has such a construction as that shown in FIG. 1. Light pulses generated by a pico-second light pulse generator 1 are split by a beam splitter 2 into two, one is applied via an optical delay line 8 to a Kerr shutter 9 and the other is applied to an optical fiber 3 to be measured. The Kerr shutter 9 comprises polarizers 4 and 5, which are disposed parallel to each other, and a Kerr cell 6, the Kerr cell 6 is filled with a material which causes birefringence due to the light-Kerr effect. Only when the light pulses from the optical delay line 8 are incident on the Kerr cell 6, the material in the Kerr cell achieves birefringence to open the Kerr shutter 9, receiving the light pulses from the optical fiber 3 by the photo detector 7. The optical delay line 8 formed, for example, by a prism, is moved so that the incidence of the light pulses from the optical fiber 3 to the Kerr shutter 9 may coincide with the opening of the Kerr shutter 9 to receive the maximum power of the light, and the delay of the pulse relative to a reference value is measured, for each wavelength, on the basis of the distance of movement of the optical delay line 8 from its reference position. The dispersion characteristic of the optical fiber is obtained from the measured value. With the prior art measuring apparatus, however, the output light from the optical fiber cannot be efficiently passed through the Kerr shutter unless the power of the light pulses for opening the Kerr shutter is greater than several hundreds of MW/cm$^2$. Furthermore, since there is not available a photo detector capable of accurately measuring the power of pico-second pulses in the long wave band above 1 $\mu$m, the wavelength band to be measured is limited specifically to a band of lower than 1 $\mu$m.

The present invention will hereinafter be described in detail.

Figure 2:
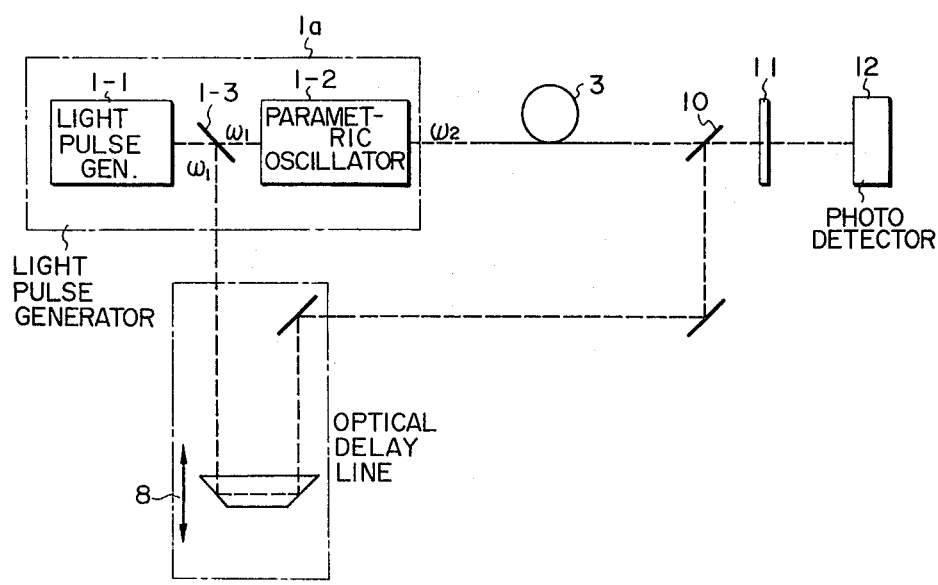

In FIG. 2, a pico-second light pulse generator 1a comprises a light pulse generator 1-1 for generating light pulses of a frequency $\omega_1$ and a variable-wavelength, parametric oscillator 1-2 using the light pulses as a light source. The light pulses of the frequency $\omega_1$ are for reference use, which pass through an optical delay line 8 and are then applied via a beam splitter 10 to a nonlinear crystal 11 such, for example, as KDP or LiIO$_3$. On the other hand, light pulses of a frequency $\omega_2$ which are obtained, using the light pulses of the frequency $\omega_1$, enter the nonlinear crystal 11 after passing through an optical fiber 3 in which dispersion is to be measured. The nonlinear crystal 11 serves as an optical nonlinear effect element which generates light pulses of frequencies $\omega_1$, $\omega_2$, $2\omega_1$ and $2\omega_2$ when input light pulses of the frequencies $\omega_1$ and $\omega_2$ are not superimposed on each other in the nonlinear crystal 11, but yields high-intensity light pulses of a frequency $(\omega_1+\omega_2)$ other than the light pulses of the abovesaid frequencies when the two input light pulses are superimposed on each other in the nonlinear crystal 11. Since the frequencies $\omega_1$ and $\omega_2$ are preknown, it is possible to obtain the time point of superimposition of the two pulses by moving the optical delay line 8 while watching the output power at the frequency $(\omega_1+\omega_2)$ alone. Next, by changing the frequency $\omega_2$ by $\Delta\omega$ and applying light pulses of a frequency $(\omega_2+\Delta\omega)$ to the optical fiber 3, the delays of the light pulses of the frequencies $\omega_2$ and $(\omega_2+\Delta\omega)$ differ from each other due to the dispersion characteristic of the optical fiber 3, and the two pulses are no longer superimposed on each other in the nonlinear crystal 11. Then, the optical delay line 8 is moved to obtain the time point of superimposition of the two pulses, paying attention to an output power at a frequency $(\omega_1+\omega_2+\Delta\omega)$. If the position of the optical delay line 8 in this case is deviated from its previous position, for example by a distance L, then a difference in delay between the light pulses of the frequencies $\omega_2$ and $(\omega_2+\Delta\omega)$ can be obtained from L/C (C: velocity of light). Since the value L of the distance can be measured accurately to several tens of microns, the delay can be measured with an accuracy of less than pico-seconds. In this way, by changing the light pulse frequency $\omega_2$, the delay differences among respective frequencies can be measured and the dispersion of light can be obtained from the measured values.

Figure 3A:
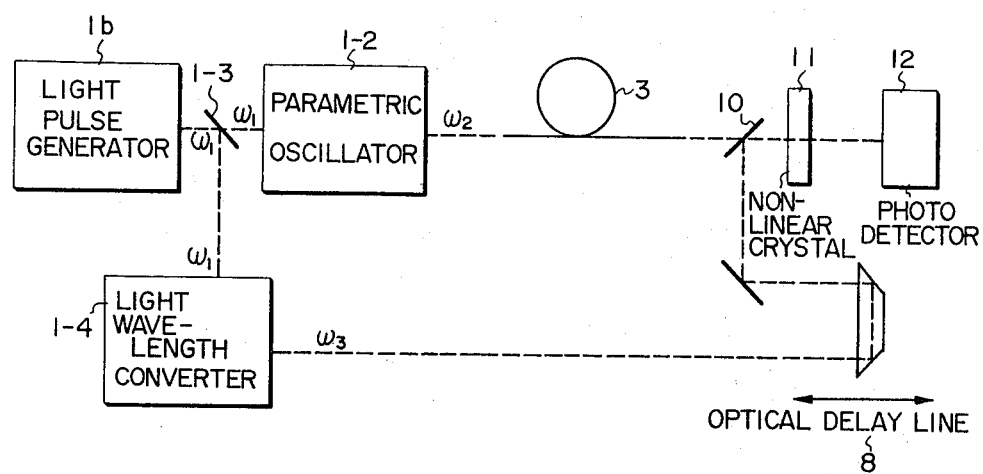
Figure 3B:
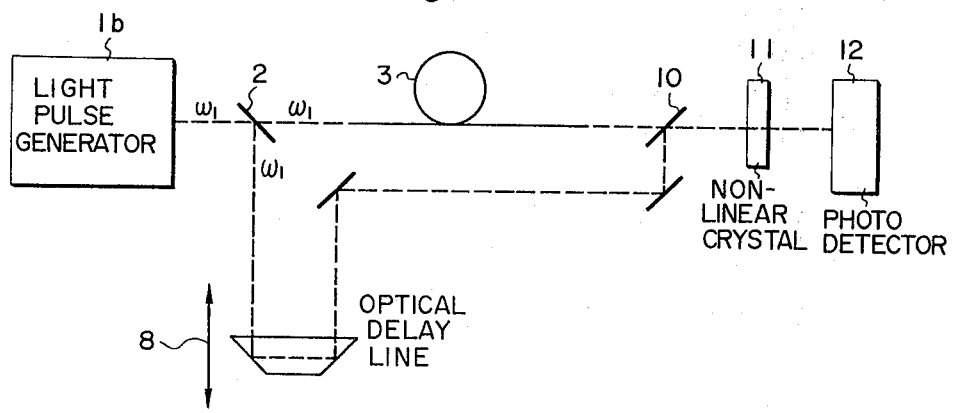

The light source for the reference pulse is fixed at the frequency $\omega_1$ in FIG. 2, but it is also possible to convert $\omega_1$ to $\omega_3$ by a wavelength converter 1-4, such as an optical parametric oscillator, provided in the optical path for the reference light pulse, as shown in FIG. 3A, or to set the light pulse of the frequency $\omega_1$ to the same frequency as the reference pulse, as shown in FIG. 3B.

Figure 4:
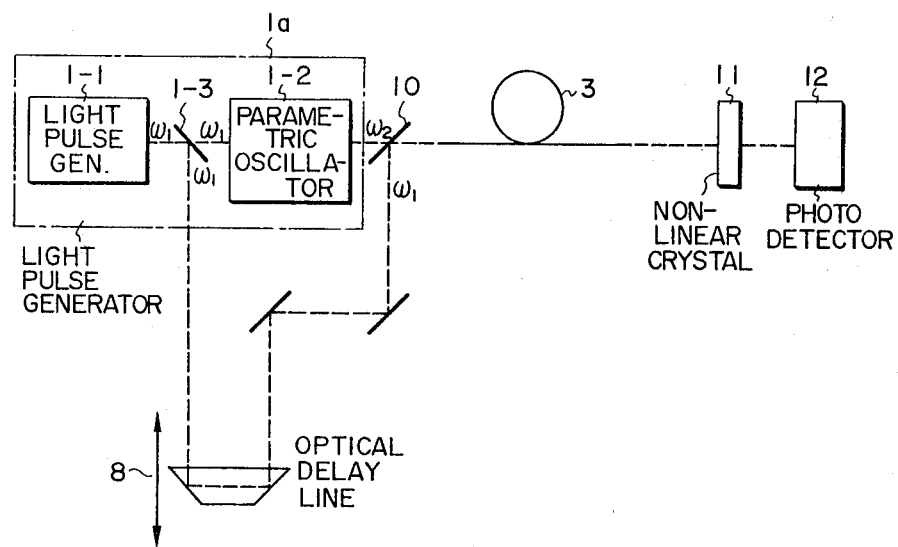

Further, in FIG. 2, the light pulse for reference use is guided directly to the nonlinear crystal 11 without passing through the optical fiber 3, but in a case where respective light pulses are of different frequencies, the light pulse for reference use may also be passed through the optical fiber 3 as is the case with the light pulse for measuring use, as shown in FIG. 4.

It is known in the art that a single mode fiber which has only one propagation mode varies its propagation velocity according to the plane of polarization, and the velocity variations are theoretically as small as 10 to 20 pico-seconds/km and cannot be measured with use of a small-length fiber, but such small velocity variations can be measured by the equipment of the present invention. In addition, the percentage of elongation of the optical fiber by tension in a case of using a small-length fiber can also be measured accurately through utilization of this equipment.

As has been described in the foregoing, according to the present invention, since the nonlinear crystal is employed as a wavelength converter and a pico-second shutter, it is possible to measure, with high accuracy, dispersion in the 1 $\mu$m band which could not have been measured through the use of pico-second pulses and, in addition, since the peak power of the pulses used may be about several kW/cm$^2$, the measuring apparatus of the present invention is easy to handle.

What we claim is:

1. A light dispersion measuring apparatus comprising: a light source for generating reference light pulses each having a short duration and at a constant frequency and generating variable-frequency light pulses in synchronization with the reference light pulses and at a different frequency than the reference light pulses, a variable optical delay line for receiving and delaying the reference light pulses, an optical light transmission medium the light dispersion characteristic of which is to be measured and to which the variable-frequency light pulses and delayed reference light pulses from the optical delay line are applied, an optical nonlinear effect element for receiving the output light pulses from the optical transmission medium disposed so that when timing of the delayed reference light pulses and the variable frequency light pulses coincide with each other, a sum of the light of coincident pulses is at a maximum sum light intensity in in output pulses from the optical nonlinear effect element, a photo detector receptive of the last-mentioned output pulses for detecting the value of the sum light intensity thereof, and the light dispersion characteristic in the optical transmission medium is measured from the delay of the variable optical delay line when adjusted so that said maximum light intensity occurs with respect to the frequency of the variable-frequency light pulses.

2. A light dispersion measuring apparatus according to claim 1, in which said optical nonlinear effect element is nonlinear crystal.

3. A light dispersion measuring apparatus according to claim 2, in which said nonlinear crystal is a light wavelength converter and a pico-second shutter functioning with the application of pico-second pulses, thereby measuring light dispersion in a 1 $\mu$m band.

* * * * *